(12) United States Patent
Stehr et al.

(10) Patent No.: US 8,728,055 B2
(45) Date of Patent: May 20, 2014

(54) BRAIDED PEELABLE SHEATH

(75) Inventors: Richard E. Stehr, Stillwater, MN (US); Xiaoping Guo, Eden Prairie, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 844 days.

(21) Appl. No.: 11/910,503

(22) PCT Filed: Jun. 14, 2006

(86) PCT No.: PCT/US2006/023136
§ 371 (c)(1),
(2), (4) Date: Oct. 2, 2007

(87) PCT Pub. No.: WO2006/138356
PCT Pub. Date: Dec. 28, 2006

(65) Prior Publication Data
US 2009/0043285 A1    Feb. 12, 2009

Related U.S. Application Data

(60) Provisional application No. 60/690,270, filed on Jun. 14, 2005.

(51) Int. Cl.
*A61M 25/00* (2006.01)
*A61M 25/06* (2006.01)
*A61M 25/01* (2006.01)

(52) U.S. Cl.
CPC ......... *A61M 25/005* (2013.01); *A61M 25/0668* (2013.01); *A61M 2025/0188* (2013.01)
USPC ..................................... 604/527; 604/164.05

(58) Field of Classification Search
CPC .......... A61M 25/005; A61M 25/0108; A61M 25/0668; A61M 2025/0188
USPC ...................... 604/160, 161, 164.05, 523–527
See application file for complete search history.

(56) References Cited

U.S. PATENT DOCUMENTS

| 4,402,685 A | * | 9/1983 | Buhler et al. | ................. 604/523 |
| 4,983,168 A | | 1/1991 | Moorehead | |
| 5,104,388 A | | 4/1992 | Quackenbush | |

(Continued)

FOREIGN PATENT DOCUMENTS

| DE | 4221820 A1 | 1/1994 |
| EP | 0279015 A2 | 8/1988 |
| WO | 97/40880 A1 | 11/1997 |

OTHER PUBLICATIONS

Extended European Search Report, EP 06773143, dated Sep. 14, 2009.

*Primary Examiner* — Kami A Bosworth
(74) *Attorney, Agent, or Firm* — Wiley Rein LLP

(57) ABSTRACT

The present invention is a splitable/peelable reinforced flexible tubular body (10) for a catheter or sheath (12). The body (10) comprises a proximal end (14), a distal end (16), a wall structure (18), and a lumen (20) defined by the wall structure (18). The wall structure (18) extends between the ends and includes a reinforcement layer (22) within the wall structure (18) and a separation line (26) extending longitudinally along the wall structure (18). The separation line (26) is adapted to facilitate the splitting/peeling of the wall structure (18) to allow a medical device such as a pacemaker lead to be removed from within the tubular body (10).

12 Claims, 9 Drawing Sheets

(56) References Cited

U.S. PATENT DOCUMENTS

| | | | |
|---|---|---|---|
| 5,713,867 A | * 2/1998 | Morris | 604/164.05 |
| 6,887,417 B1 | 5/2005 | Gawreluk et al. | |
| 2004/0267203 A1 | 12/2004 | Potter et al. | |
| 2005/0182387 A1 | * 8/2005 | Webler | 604/527 |

* cited by examiner

Place two inner tube sections on a mandrel wherein said sections are separated by a pair of gaps.
[block 400]

Place extruded sections of a polymer material that is dissimilar to the polymer material utilized for the inner tube sections in the gaps between the inner tube sections.
[block 402]

Place a reinforcement layer over or about the outer circumferential surface of the inner tube sections.
[block 404]

Pre-stress or pre-treat the reinforcement layer to fail along a line on the reinforcement layer that corresponds and aligns with the separation line to be formed in the tubular body.
[block 406]

Place two outer tube sections over the reinforcement layer such that the gaps between the outer tube sections align with the gaps between the inner tube sections.
[block 408].

⇨

Place extruded sections of a polymer material that is dissimilar to the polymer material utilized for the outer tube sections in the gaps between the outer tube sections.
[block 410]

Place a shrink tube snuggly over the outer circumferential surface of the assembly comprising the mandrel, the inner tube sections, the reinforcement layer, the outer tube sections, and the polymer extrusions.
[block 412].

Apply heat to the shrink tube covered assembly, thereby causing the outer tube sections to impregnate the reinforcement layer and bond with the inner tube sections, and the extrusions to bond with the inner and outer tube sections to form the separation lines.
[block 414].

Remove the shrink tube from the resulting flexible tubular body, which now has a reinforced wall structure that is readily separable along a separation line or strip.
[block 416]

FIG. 28

Place two inner tube sections on a mandrel wherein said sections are separated by a pair of gaps and said mandrel has ridges for forming peel grooves in the flexible tubular body.
[block 500]

Place a reinforcement layer over or about the outer circumferential surface of the inner tube sections.
[block 502]

Pre-stress or pre-treat the reinforcement layer to fail along a line on the reinforcement layer that corresponds and aligns with the separation line to be formed in the tubular body.
[block 504]

Place two outer tube sections over the reinforcement layer such that the gaps between the outer tube sections align with the gaps between the inner tube sections.
[block 506].

Place a shrink tube snuggly over the outer circumferential surface of the assembly comprising the mandrel, the inner tube sections, the reinforcement layer, the outer tube sections, and the polymer extrusions.
[block 508].

Apply heat to the shrink tube covered assembly, thereby causing the outer tube sections to impregnate the reinforcement layer and bond with the inner tube sections, the ridges of the mandrel forming peel grooves aligned with the separation lines.
[block 510].

Remove the shrink tube from the resulting flexible tubular body, which now has a reinforced wall structure that is readily separable along separation lines defined by peel grooves formed in said wall structure.
[block 512]

FIG. 29

BRAIDED PEELABLE SHEATH

CROSS-REFERENCE TO RELATED APPLICATIONS

The present application claims the benefit to U.S. Provisional Patent Application No. 60/690,270 ("the '270 application"), which was filed on 14 Jun. 2005. The '270 application is hereby incorporated by reference as though fully set forth herein.

FIELD OF THE INVENTION

The present invention relates to catheters and sheaths and methods of making and using catheters and sheaths. More particularly, the present invention relates to the flexible tubular bodies of steerable catheters or sheaths and methods of making and using such bodies.

BACKGROUND OF THE INVENTION

Catheters and sheaths having flexible tubular bodies with reinforced wall structures are utilized for introducing, positioning and implanting medical devices (e.g., pacemaker leads) within a patient. Once a medical device is implanted within a patient, the catheter or sheath must be withdrawn without causing displacement of the implanted medical device. Often, as in the case of pacemaker leads, this requires that the wall structure of the catheter or sheath be split.

While a catheter or sheath with a reinforced wall structure offers superior ability to withstand the compression, tension and torque forces exerted on a catheter or sheath during a medical procedure, the wall structures of such catheters or sheaths are not readily splitable. As a result, a physician must physically cut the reinforced wall structure of such catheters or sheaths. This increases the difficulty and time requirement for a medical procedure.

There is a need in the art for a flexible tubular body with a reinforced wall structure that is readily splitable. There is also a need in the art for a method of manufacturing such a flexible tubular body.

BRIEF SUMMARY OF THE INVENTION

The present invention, in one embodiment, is a splitable reinforced flexible tubular body for a catheter or sheath. The body comprises a proximal end, a distal end, a wall structure, and a lumen defined by the wall structure. The wall structure extends between the ends and includes a reinforcement layer within the wall structure and a separation line extending longitudinally along the wall structure. The separation line is adapted to facilitate the splitting of the wall structure to allow a medical device such as a pacemaker lead to be removed from within the tubular body.

In one embodiment, the reinforcement layer is a mesh or braid layer. In one embodiment, the separation line is a strip of a first polymer material that is different from a second polymer material utilized to form the rest of the wall structure. The bond interface between the first and second polymer materials creates a stress concentration that facilitates the splitting of the wall structure.

In one embodiment, the first polymer material is more radiopaque than the second polymer material. For example, in one embodiment, the first polymer material is a polymer loaded a with biocompatible radiopaque filler of pure metal or metallic compound with at least one atomic number of from about 22 to about 83. In one embodiment, the first polymer material is a polymer loaded with tungsten.

In one embodiment, the separation line is formed by severing the wall structure and its reinforcement layer to form a longitudinally extending gap. A strip of the first polymer material is then inserted into the gap and caused to bond to the second polymer material.

In one embodiment, the reinforcement layer is pre-stressed or pre-treated to fail along a longitudinal path that aligns with the separation line. A strip of the first polymer material is then bond to the second polymer material to form an integral wall structure.

In one embodiment, the separation line is defined by a peel groove longitudinally extending along the wall structure. In one embodiment, the separation line is formed by severing the wall structure and its reinforcement layer to form a longitudinally extending gap. The gap is then aligned with a peel groove forming feature on a mandrel, and the wall structure is heated to cause the wall structure to rejoin at the gap while forming the peel groove.

In one embodiment, the reinforcement layer is pre-stressed or pre-treated to fail along a longitudinal path that aligns with the peel groove that defines the separation line.

The present invention, in one embodiment, is a method of manufacturing a splitable reinforced flexible tubular body for a catheter or sheath. The method comprises providing a reinforced flexible tubular body including a wall structure defining a lumen and including an integral reinforcement layer, longitudinally splitting the wall structure to form a gap therein defined by first and second longitudinal edges of the wall structure, and joining the first and second edges together to eliminate the gap.

In one embodiment, joining the first and second edges includes subjecting the tubular body to a heat source. In one embodiment, a layer of heat shrink material is placed about an outer circumferential surface of the wall structure.

In one embodiment, the wall structure is placed on a mandrel including a ridge for forming a longitudinally extending peel groove in an interior circumferential surface of the wall structure. The wall structure is positioned about the mandrel such that the ridge is generally aligned with the gap.

In one embodiment, prior to subjecting the wall structure to a heat source, a first polymer material, which is at least somewhat different in composition from the a second polymer material used to form the wall structure, is place in the gap. The heat source creates a bond interface between the first and second polymer materials, which creates a stress concentration that facilitates the splitting of the wall structure.

In one embodiment, the first polymer material is more radiopaque than the second polymer material. In one embodiment, the first polymer material is a polymer loaded with biocompatible radiopaque filler of pure metal or metallic compound with at least one atomic number of from about 22 to about 83. In one embodiment, the first polymer material is a polymer loaded with tungsten.

The present invention, in one embodiment, is a method of manufacturing a splitable reinforced flexible tubular body for a catheter or sheath. The method comprises: providing an inner tube about a mandrel, wherein the inner tube is longitudinally split to form a first gap defined by first and second longitudinal edges of the inner tube; providing a reinforcement layer about the outer circumferential surface of the inner tube; providing an outer tube about the reinforcement layer, wherein the outer tube is longitudinally split to form a second gap defined by third and fourth longitudinal edges of the outer tube, wherein the outer tube in positioned such that the second gap generally aligns with the first gap; providing a heat shrink layer about the outer circumferential surface of the outer layer; and applying heat to the heat shrink layer to cause the joining of the inner and outer tubes, the first and second edges, and the third and fourth edges.

In one embodiment, the mandrel includes a ridge for forming a longitudinally extending peel groove in an interior circumferential surface of the inner tube. The inner tube is positioned about the mandrel such that the ridge is generally aligned with the first gap.

In one embodiment, the method includes placing a first polymer material in the first and second gaps that is at least somewhat different in composition from the a second polymer material used to form the inner and outer tubes. In one embodiment, the heat source creates a bond interface between the first and second materials, which creates a stress concentration that facilitates the splitting of the tubular body. In one embodiment, the first polymer material is more radiopaque than the second polymer material. In one embodiment, the first polymer material is a polymer loaded with biocompatible radiopaque filler of pure metal or metallic compound with at least one atomic number of from about 22 to about 83. In one embodiment, the first polymer material is a polymer loaded with tungsten.

In one embodiment, the method includes adapting the reinforcement layer to fail along a longitudinal fail line that is aligned with the first gap. In one embodiment, the reinforcement layer is stressed or treated along the longitudinal fail line prior to being placed about the outer circumferential surface of the inner tube. In one embodiment, the reinforcement layer is stressed or treated along the longitudinal fail line after being placed about the outer circumferential surface of the inner tube.

In one embodiment, the reinforcement layer is stressed or treated by a method selected from the group consisting of fatiguing, heat treating and chemical treating a mesh or a plurality of braids forming the reinforcement layer. In one embodiment, the reinforcement layer is stressed or treated by a method selected from the group consisting of pinching, crushing, and nicking a mesh or a plurality of braids forming the reinforcement layer.

In one embodiment, the reinforcement layer includes a mesh or a plurality of braids and the reinforcement layer is stressed or treated by cutting the braids or mesh at intervals along the longitudinal fail line. In one embodiment, the reinforcement layer is configured to: resist forces tending to crush, kink, twist, longitudinally compress, or longitudinally stretch the tubular body; and fail in the vicinity of the first gap when sides of the tubular body opposite from each other across the first gap are forced laterally apart from each other.

The present invention, in one embodiment, is a splitable flexible tubular body for a catheter or sheath as disclosed in the prior U.S. Provisional Patent Application No. 60/675,973, which was filed on 28 Apr. 2005, entitled "Splittable Tubular Body For A Catheter Or Sheath", and further disclosed in international patent application no. PCT/US2006/016373, which was filed on 28 Apr. 2006, and in international patent application no. PCT/2006/016373, which was also filed on 28 Apr. 2006. Said provisional patent application and PCT applications are hereby incorporated by reference in their entireties into the present application.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

BRIEF DESCRIPTION OF THE DRAWINGS

FIG. 28 is a block diagram outlining the method of manufacturing the flexible tubular body embodiments illustrated in FIGS. 16-21.

FIG. 29 is a block diagram outlining the method of manufacturing the flexible tubular body embodiments illustrated in FIGS. 22-27.

DETAILED DESCRIPTION

The present invention, in one embodiment, is a flexible tubular body 10 for a steerable catheter, sheath or similar medical device 12. The tubular body 10 is reinforced to withstand forces arising from compression, tension and torque. Additionally and advantageously, the tubular body 10 is configured to be readily splitable/peelable. The splitable/peelable feature of this reinforced tubular body 10 allows the removal of such medical devices as pacemaker leads from the tubular body 10.

Figure 1:
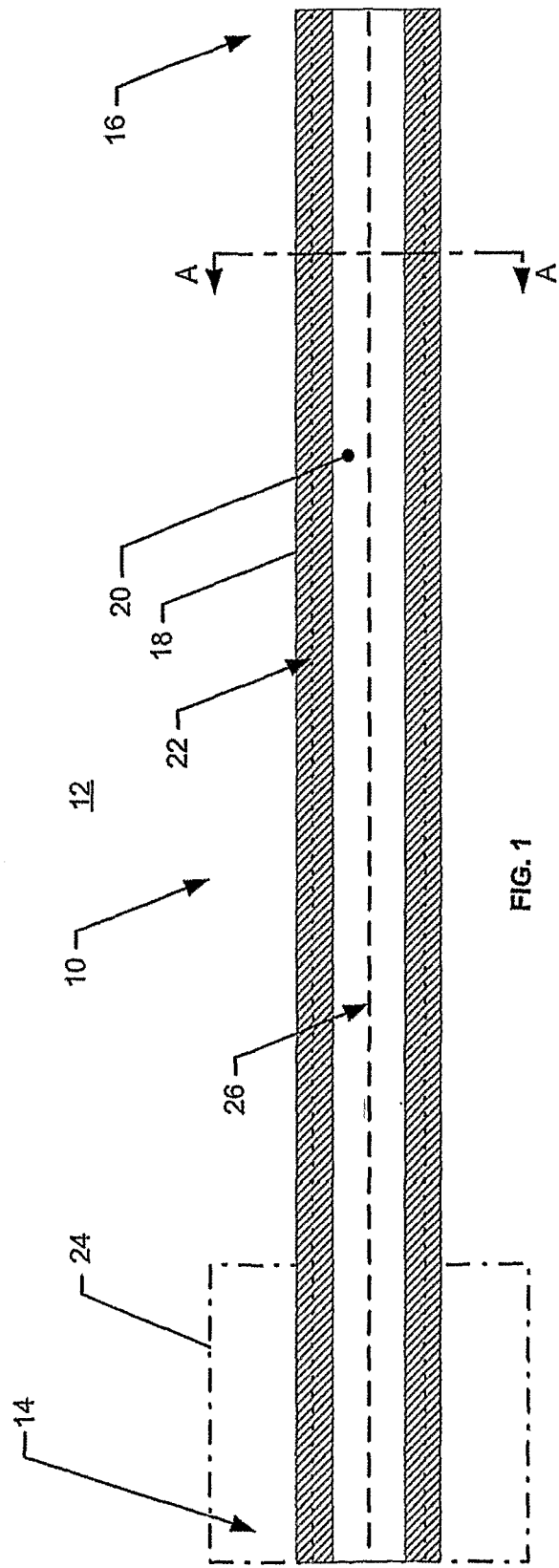
FIG. 1 is a longitudinal cross-sectional side elevation of a catheter, sheath or similar device employing the flexible tubular body of the subject invention.

For a discussion of the splitable/peelable reinforced tubular body 10 of the subject invention, reference is made to FIG. 1, which is a longitudinal cross-sectional side elevation of a catheter, sheath or similar device 12 employing the body 10 of the subject invention. As shown in FIG. 1, in one embodiment, the catheter or sheath 12 includes a generally tubular flexible body 10. The flexible body 10 includes a proximal end 14, a distal end 16, a wall structure 18, and a lumen 20. The proximal end 14 may be grasped by a physician to manipulate the body 10 during the performance of a medical procedure. The distal end 16 is adapted to enter a patient. The wall structure 18 includes an integral reinforcement layer 22 that helps the body 10 to resist the compression, tension and torque forces that arise during the performance of a medical procedure. The lumen 20 is defined by the wall structure 18 and extends the length of the flexible body 10.

In one embodiment, an actuation handle 24 is coupled to the proximal end 14 and the distal end 16 is adapted to deflect (i.e., bend) when actuated by the handle 24. As disclosed in detail in U.S. patent application Ser. No. 11/023,667, which was filed Dec. 28, 2004, entitled "Bi-Directional Steerable Catheter Control Handle", and hereby incorporated by reference in its entirety into this present application, one or more deflection wires extend through the body 10 from the handle 24 to a point near the distal 16 end of the body 10.

As indicated in FIG. 1, the tubular body 10 includes one or more separation lines or strips 26 that extend along the length of the body 10 from the distal end 16 to the proximal end 14. The wall structure 18 at a separation line 26 is configured such that the reinforcement layer 22 and the rest of the associated wall structure 18 aligned with the separation line 26 are adapted to separate along the separation line 26. For example, in a first embodiment of the tubular body 10, the reinforcement layer 22 is severed along the separation line 26 prior to the final assembly of the tubular body 10. In a second embodiment, the reinforcement layer 22 is not severed prior to final assembly, but is instead pre-stressed or pre-treated along the separation line 26 prior to final assembly of the tubular body 10. In either case, the reinforcement layer 22 and the rest of the associated wall structure 18 aligned with the separation line 26 are adapted to fail along the separation line 26, thereby allowing the tubular body 10 to be opened along the separation line 26 to allow the removal of pacemaker leads or other medical devices from the body 10.

Figure 14:
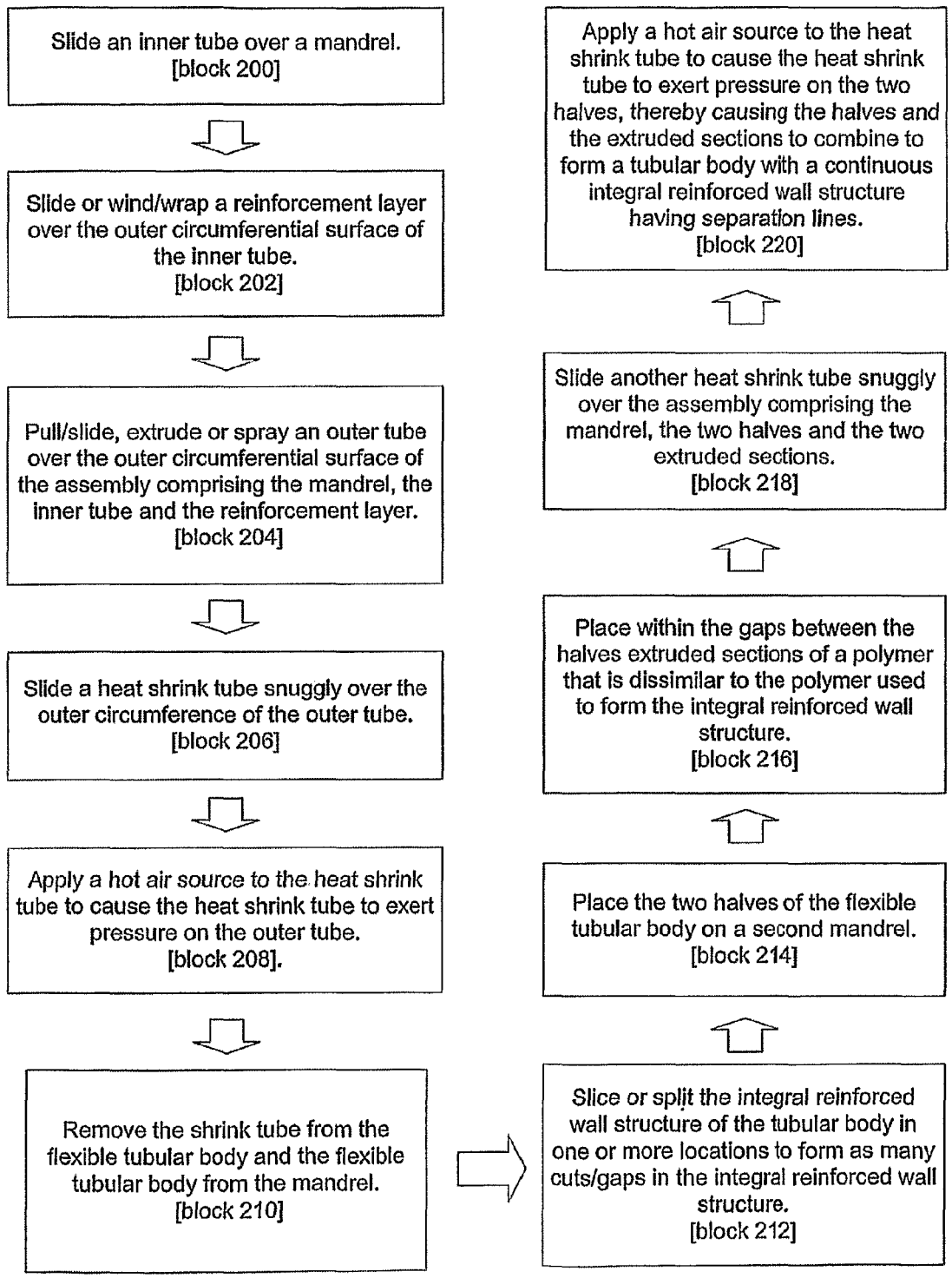
FIG. 14 is a block diagram outlining the method of manufacturing the flexible tubular body embodiments illustrated in FIGS. 2-7.

For a discussion of a method of manufacturing the first embodiment of the tubular body 10, reference is now made to FIGS. 2-7 and 14. FIGS. 2-7 are latitudinal cross-sectional elevations of the tubular body 10 at various stages of the manufacturing process as if taken along section line AA in FIG. 1. FIG. 14 is a block diagram outlining the method pertaining to FIGS. 2-7.

Figure 2:
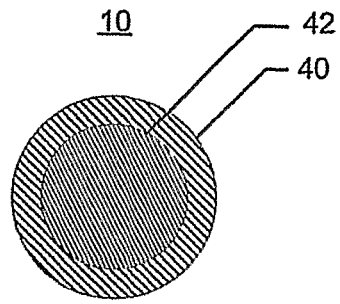
FIG. 2 is a latitudinal cross-sectional elevation of an inner tube of the tubular body as it is being manufactured on a mandrel and as if taken along section line AA in FIG. 1.

As indicated in FIG. 2, an inner tube 40 with a wall thickness of approximately 0.0015-0.003 inches is slid over a mandrel 42 [block 200]. In one embodiment, the inner tube 40 is pre-extruded from a thermoplastic polymer (e.g., polytetrafluoroethylene "PTFE", polyvinylidene fluoride "PVDF", polyetheretherketone "PEEK", etc.).

Figure 3:
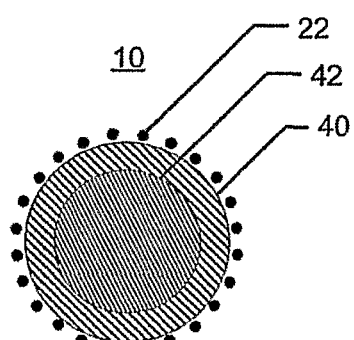
FIG. 3 is the same view depicted in FIG. 2, except a reinforcement layer has been disposed about the outer circumferential surface of the inner tube.

As illustrated in FIG. 3, a reinforcement layer 22 is slid over or wound/wrapped about the outer circumferential surface of the inner tube 40 [block 202]. In one embodiment, the reinforcement layer 22 is a braided or mesh layer made of stainless steel wire. The stainless steel wire may have a circular cross-section of between about 0.0010 inches and about 0.0050 inches. Alternatively, a flat wire could be used. In one embodiment, the flat wire is about 0.00075 inches by about 0.005 inches. In one embodiment, the wire is ELGILOY® nickel-cobalt alloy. In one embodiment, the reinforcement layer 22 is a mesh or braided layer made of carbon fiber, glass fiber, polymeric materials, or other non-metallic materials.

Figure 4:
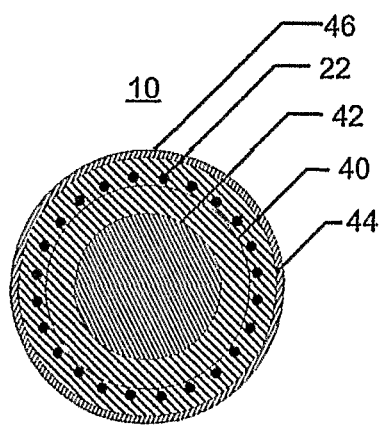
FIG. 4 is the same view depicted in FIG. 3, except a heat shrink tube has been used to heat shrink an outer tube about the inner tube and reinforcement layer to form a flexible tubular body with an integral wall structure.

As shown in FIG. 4, an outer tube 44 is pulled/slid, extruded or sprayed over the outer circumferential surface of the assembly comprising the mandrel 42, the inner tube 40 and the reinforcement layer 22 [block 204]. Alternatively, the outer tube 44 may be longitudinally slit and wrapped around the outer circumferential surface of said assembly. In one embodiment, the outer tube 44 is a thermoplastic polymer such as PTFE, PVDF, PEEK, etc. In another embodiment, the outer tube 44 is a thermoplastic polymer such as polyether block amide "PEBA", PVDF, polyethylene terephthalate "PET", etc.

As indicated in FIG. 4, a heat shrink tube 46 is snuggly slid over the outer circumference of the outer tube 44 [block 206]. A hot air source of about 200 degree F. to about 400 degree F. is applied to the heat shrink tube 46, which causes the heat shrink tube 46 to exert pressure on the outer tube 44 [block 208]. The combination of heat and pressure causes the outer tube 44 to melt into the reinforcement layer 22 and bond to the inner tube 40, thereby forming a single integral reinforced wall structure 18. In one embodiment, the outer circumferential surface of the inner tube 40 is etched to enhance bonding between the inner and outer tubes 40, 44.

Outright chemical compatibility between the various polymeric materials or surface modification to achieve reliable surface bonding is necessary to ensure that the tubular body 10 is fully laminated during the lamination process into an integrated structure in the form of interfacial bonding by means of liquefying the inner and outer tubes 40, 44. When heat is applied, the heat shrink tube 46 starts to generate varying lamination pressure, which transfers inwards thermal energy to liquefy the outer layer 44 during the lamination process.

In one embodiment, the heat shrink tube 46 is a polymeric material such as fluorinated ethylene-propylene copolymer "FEP", PTFE, or PET. In one embodiment, the heat shrink tube 46 has a shrink temperature ranging from approximately 190 degrees F. to approximately 220 degrees F.

To ensure that the outer layer 44 is completely liquefied during the lamination process, the shrink temperature of the heat shrink tube 46 must be higher than the softening or melting temperature of the outer layer 44. The combination of heat and pressure during lamination results in a flexible tubular body 10 with an integral reinforced wall structure 18 via polymer melt flow and interfacial bonding among all laminated components.

As shown in FIG. 4, the mandrel 42 supports the central lumen 20 during the lamination process. This prevents the lumen 20 from collapsing from the heat and pressure.

Figure 5:
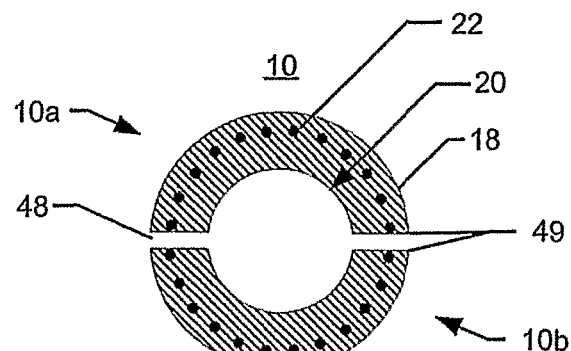
FIG. 5 is the same view depicted in FIG. 4, except the heat shrink tube has been removed from the flexible tubular body, said body has been removed from the mandrel, and the integral wall structure has been slit at two locations to form first and second halves of the flexible tubular body.

As indicated in FIG. 5, the shrink tube 46 is removed from the tubular body 10 and the body 10 is removed from the mandrel 42 [block 210]. The integral reinforced wall structure 18 of the tubular body 10 defines the lumen 20 and is sliced or split in one or more locations to form as many cuts or gaps 48 in the integral reinforced wall structure 18 [block 212]. The gaps 48 are defined by edges 49 of the wall structure 18. In one embodiment, as shown in FIG. 5, there are two cuts 48, thereby forming two separate sections 10a, 10b of the tubular body 10.

Figure 6:
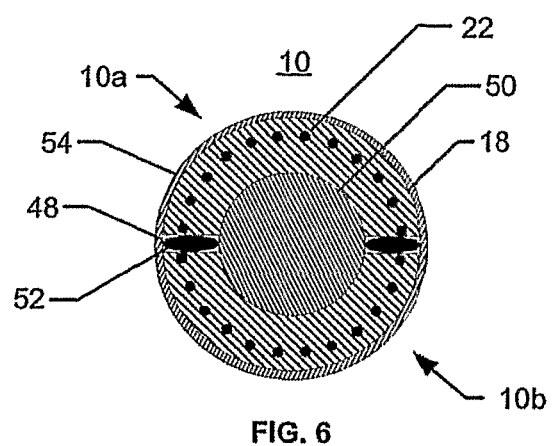
FIG. 6 is the same view depicted in FIG. 5, except strips of filler material have been placed between the adjacent ends of the first and second halves, and the first and second halves and strips have been secured about a second mandrel via a second heat shrink tube.

As illustrated in FIG. 6, the two sections 10a, 10b of the tubular body 10 are placed on a second mandrel 50 [block 214]. In one embodiment, extruded sections 52 of a polymer that is dissimilar to the polymers used to form the inner and outer tubes 40, 42 are placed within the gaps 48 between the tubular body sections 10a, 10b formed by the cuts 48 [block 216]. In one embodiment, the extruded sections 52 are 70-90% tungsten filled polymer. In other embodiments, the extruded sections 52 are other filled or unfilled polymers that are melt compatible with the base material.

As indicated in FIG. 6, another heat shrink tube 54 is snuggly slid over the assembly comprising the mandrel 50, the two body sections 10a, 10b and the two extruded sections 52 [block 218]. In one embodiment, the heat shrink tube 54 is a polymeric material such as FEP, PTFE, or PET. In one embodiment, the heat shrink tube 54 has a shrink temperature ranging from approximately 190 degrees F. to approximately 220 degrees F.

Figure 7:
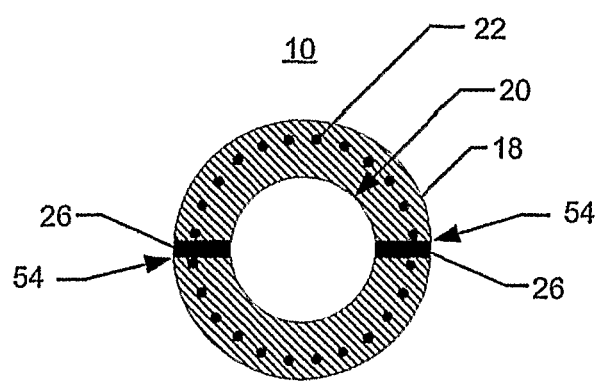
FIG. 7 is the same view depicted in FIG. 6, except the heat shrink tube has been removed from the flexible tubular body and said body has been removed from the mandrel after the strips and halves of said body have been heat shrunk into an integral wall structure.

A hot air source of about 200 degree F. to about 400 degree F. is applied to the heat shrink tube 54, which causes the heat shrink tube 54 to exert pressure on the two halves 10a, 10b [block 220]. The combination of heat and pressure causes the extruded sections 52 to melt into and bond with the edges of the tubular body sections 10a, 10b that define the gaps 48. As a result, the body sections 10a, 10b and the extruded sections 52 combine to form a tubular body 10 with a continuous integral reinforced wall structure 18 having separation lines 26, as depicted in FIGS. 1 and 7.

As can be understood from the FIGS. 1-7 and the preceding discussion, the present invention offers a flexible tubular body 10 having a reinforced integral wall structure 18 that is readily splitable via one or more separation lines or strips 26 that run longitudinally along the body 10. In use, once a medical device (e.g., a pacemaker lead) has been positioned within the patient via the catheter or sheath 12, the flexible tubular body 10 may be readily split/peeled along the separation lines 26 by simply forcing the first and second halves 10a, 10b of the body 10 away from each other via a finger nail, tool or other implement.

The readily splitable/peelable feature of the present invention is made possible by the change in material at the border/interfaces 54 between the separation strips 26 and the adjacent portions of the wall structure 18 formed by the original inner and outer tubes 40, 44. The change in material creates a stress concentration point that runs the length of the respective border/interface 54. Each stress concentration acts as built-in peel groove along which the tubular body 10 splits. Thus, a physician does not need to cut or slice the tubular body 10 in order to split the body 10 to remove a medical device such as a pacemaker lead.

In some embodiments, as indicated in the immediately preceding discussion, the change in material at the border/interfaces 54 between the separation strips 26 and the adjacent portions of the wall structure 18 is adequate to create sufficient stress concentrations that a peel groove is not needed in order to cause the tubular body 10 to split. However, in other embodiments, such as those where the extruded polymer strips 52 used to form the separation strips 26 are essentially the same material as the rest of the wall structure 18, the stress concentrations along the separation strip may be inadequate to make the tubular body 10 readily splitable. Thus, in one embodiment, to increase split ability, a peel groove 60 is molded along the separation strip 26 to facilitate the creation of adequate stress concentrations to allow the tubular body 10 to be readily split without having to be cut or sliced.

In one embodiment, as mentioned above, the separation strips 26 are formed from a polymer material highly loaded with a radiopaque material (e.g., tungsten, barium, tantalum, platinum, gold, bismuth, zirconium, niobium, titanium, bismuth oxychloride, barium sulfate, bismuth trioxide, iodine, iodide, etc. and their compounds), which gives the separation strips 26 a radiopacity that is significantly higher than the radiopacity of the polymer materials used to form the inner and outer tubes 40, 44.

Thus, in a manner similar to that disclosed in U.S. Provisional Patent Application No. 60/675,973, entitled "Splitable Tubular Body For A Catheter Or Sheath" (filed Apr. 28, 2005, incorporated by reference into the present application in its entirety), the separation strips 26 that are loaded with a highly radiopaque material allow a physician to monitor the travel and positioning of the tubular body 10 within the patient via X-ray fluoroscopy.

Figure 8:
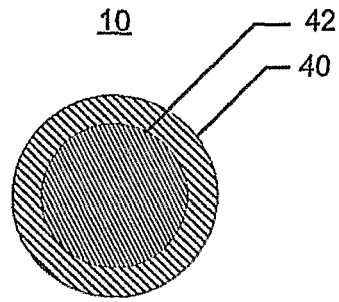
FIG. 8 is a latitudinal cross-sectional elevation of an inner tube of the tubular body as it is being manufactured on a mandrel and as if taken along section line AA in FIG. 1.
Figure 15:
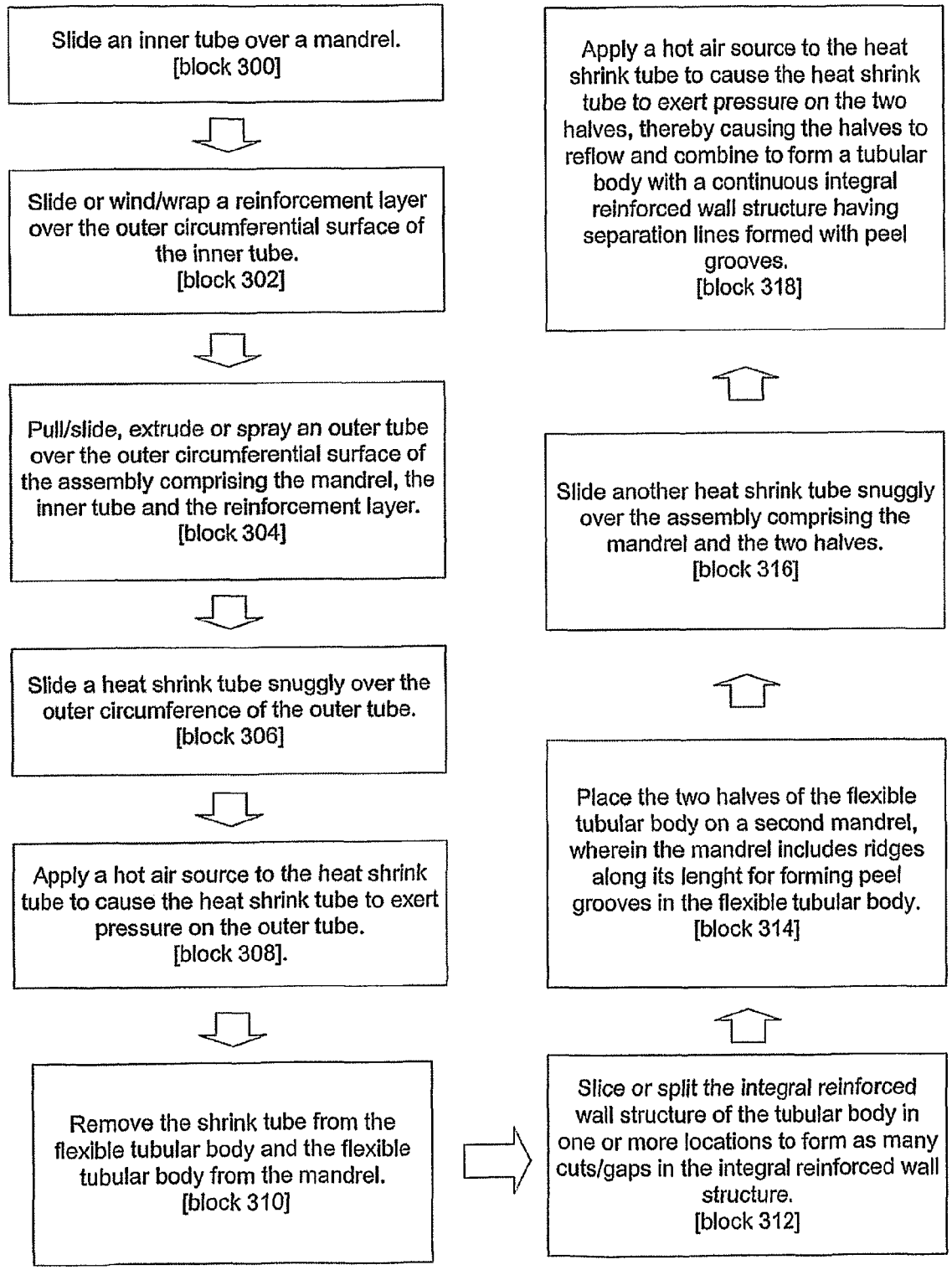
FIG. 15 is a block diagram outlining the method of manufacturing the flexible tubular body embodiments illustrated in FIGS. 8-13.

For a discussion of a method of manufacturing another version of the first embodiment of the tubular body 10, reference is now made to FIGS. 8-13 and FIG. 15. FIGS. 8-13 are latitudinal cross-sectional elevations of the tubular body 10 at various stages of the manufacturing process as if taken along section line AA in FIG. 1. FIG. 15 is a block diagram outlining the method pertaining to FIGS. 8-13. As indicated in FIG. 8, an inner tube 40, which is similar in thickness and material to those previously described in this Detailed Description, is slid over a mandrel 42 [block 300].

Figure 9:
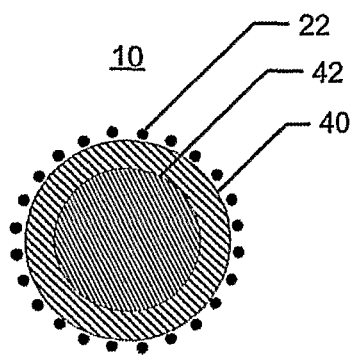
FIG. 9 is the same view depicted in FIG. 8, except a reinforcement layer has been disposed about the outer circumferential surface of the inner tube.

As illustrated in FIG. 9, a reinforcement layer 22, which is similar in configuration and material to those previously described in this Detailed Description, is slid over or wound/wrapped about the outer circumferential surface of the inner tube 40 [block 302].

Figure 10:
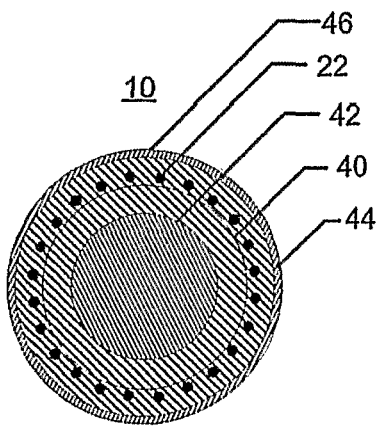
FIG. 10 is the same view depicted in FIG. 9, except a heat shrink tube has been used to heat shrink an outer tube about the inner tube and reinforcement layer to form a flexible tubular body with an integral wall structure.

As shown in FIG. 10, an outer tube 44, which is similar in thickness and material to those previously described in this Detailed Description, is pulled/slid, extruded or sprayed over the outer circumferential surface of the assembly comprising the mandrel 42, the inner tube 40 and the reinforcement layer 22 [block 304]. Alternatively, the outer tube 44 may be longitudinally slit and wrapped around the outer circumferential surface of said assembly.

As indicated in FIG. 10, a heat shrink tube 46, which is similar in thickness and material to those previously described in this Detailed Description, is snuggly slid over the outer circumference of the outer tube 44 [block 306]. A hot air source of about 200 degree F. to about 400 degree F. is applied to the heat shrink tube 46, which causes the heat shrink tube 46 to exert pressure on the outer tube 44 [block 308]. The combination of heat and pressure causes the outer tube 44 to melt into the reinforcement layer 22 and bond to the inner tube 40, thereby forming a single integral reinforced wall structure 18. In one embodiment, the outer circumferential surface of the inner tube 40 is etched to enhance bonding between the inner and outer tubes 40, 44.

Figure 11:
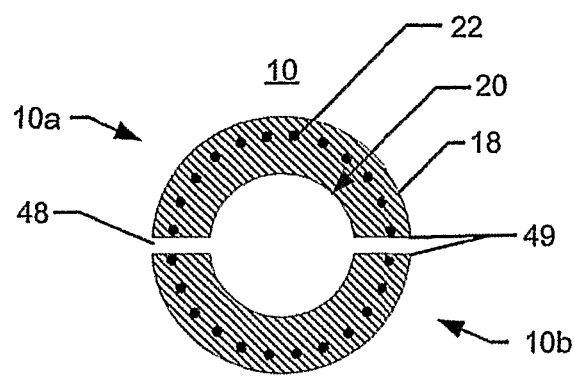
FIG. 11 is the same view depicted in FIG. 10, except the heat shrink tube has been removed from the flexible tubular body, said body has been removed from the mandrel, and the integral wall structure has been slit at two locations to form first and second halves of the flexible tubular body.

As indicated in FIG. 11, the shrink tube 46 is removed from the tubular body 10 and the body 10 is removed from the mandrel 42 [block 310]. The integral reinforced wall structure 18 of the tubular body 10 defines the lumen 20 and is sliced or split in one or more locations to form as many cuts or gaps 48 in the integral reinforced wall structure 18 [block 312]. The gaps 48 are defined by edges 49 of the wall structure 18. In one embodiment, as shown in FIG. 11, there are two cuts 48, thereby forming two separate sections 10a, 10b of the tubular body 10.

Figure 12:
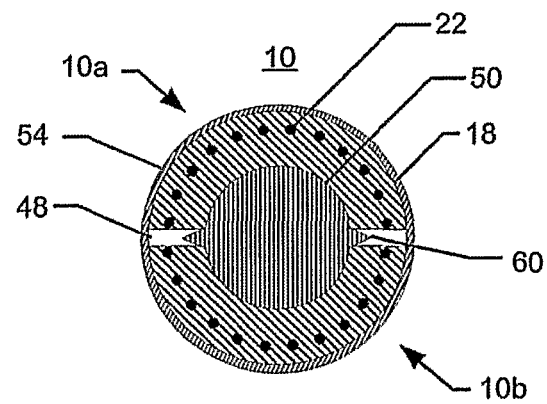
FIG. 12 is the same view depicted in FIG. 11, except the first and second halves and strips have been secured about a second mandrel via a second heat shrink tube.

As illustrated in FIG. 12, the two sections 10a, 10b of the tubular body 10 are placed on a second mandrel 50 [block 314]. As shown in FIG. 12, the second mandrel 50 includes ridges 60 that extend into the gaps 48 between the ends of the two separate sections 10a, 10b of the tubular body 10.

As indicated in FIG. 12, another heat shrink tube 54, which is similar in thickness and material to those previously described in this Detailed Description, is snuggly slid over the assembly comprising the mandrel 50 and the two sections 10a, 10b [block 316] of the tubular body 10.

Figure 13:
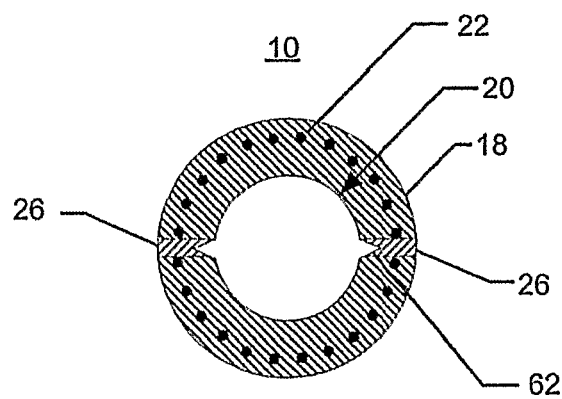
FIG. 13 is the same view depicted in FIG. 12, except the heat shrink tube has been removed from the flexible tubular body and said body has been removed from the mandrel after the halves of said body have been heat shrunk into an integral wall structure and ridges on the mandrel have formed peel grooves in said wall structure.

A hot air source of about 200 degree F. to about 400 degree F. is applied to the heat shrink tube 54, which causes the heat shrink tube 54 to exert pressure on the two sections 10a, 10b of the tubular body 10 [block 318]. The combination of heat and pressure causes the two sections 10a, 10b of the body 10 to melt and reflow to fill the gaps 48. As a result, the two sections 10a, 10b combine to form a tubular body 10 with a continuous integral reinforced wall structure 18 having a peel groove 62 along the separation lines 26, as depicted in FIGS. 1 and 13. The peel groove 62 creates sufficient stress concentrations to cause the tubular body 10 to be readily splitable along a separation line 26.

For a discussion of a method of manufacturing the second embodiment of the tubular body 10, wherein the reinforcement layer 22 is not completely severed prior to final assembly, but is instead pre-stressed or pre-treated along the separation line or strip 26, reference is now made to FIGS. 16-21 and 28. FIGS. 16-21 are latitudinal cross-sectional elevations of the tubular body 10 at various stages of the manufacturing process as if taken along section line AA in FIG. 1. FIG. 28 is a block diagram outlining the method pertaining to FIGS. 16-21.

Figure 16:
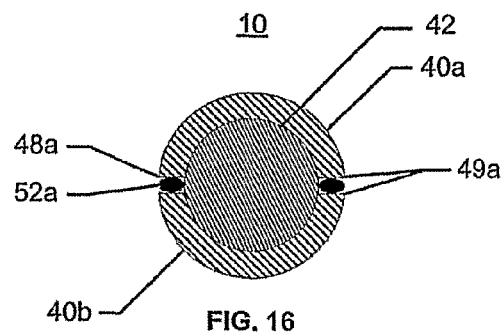
FIG. 16 is a latitudinal cross-sectional elevation of a pair of inner tube sections of the tubular body as the body is being manufactured on a mandrel and as if taken along section line AA in FIG. 1.

As shown in FIG. 16, an inner tube 40 of a flexible tubular body 10, which is similar in thickness and material to those previously described in this Detailed Description, is placed over a mandrel 42 [block 400]. In one embodiment, the inner tube 40 will have a single cut or gap 48a running the length of the tube 40. In another embodiment, the inner tube 40 will have two or more cuts or gaps 48a forming two or more inner tube sections 40a, 40b. For example, as illustrated in FIG. 16, where an inner tube 40 has two cuts or gaps 48a, the inner tube 40 will comprise two inner tube sections 40a, 40b. The gaps 48a are defined by edges 49a of the inner tube sections 40a, 40b.

As indicated in FIG. 16, extruded sections 52a of a polymer material that is dissimilar to the polymer material utilized for the inner tube sections 40a, 40b are placed in the gaps 48a [block 402]. The configuration and material of the extruded sections 52a are similar to those previously described in this Detailed Description.

Figure 17:
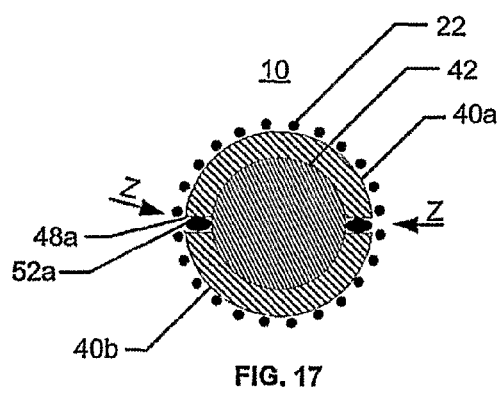
FIG. 17 is the same view depicted in FIG. 16, except a reinforcement layer has been disposed about the outer circumferential surface of the inner tube sections.

As shown in FIG. 17, a reinforcement layer 22, which is similar in configuration and material to those previously described in this Detailed Description, is slid over or wound/wrapped about the outer circumferential surface of the inner tube sections 40a, 40b [block 404].

In one embodiment, the reinforcement layer 22 is pre-stressed or pre-treated to fail along a line on the reinforcement layer 22 that corresponds and aligns with the separation line 26 to be formed in the tubular body 10 [block 406]. In other words, the reinforcement layer 22 is pre-stressed or pre-treated to fail in the area identified by each arrow Z in FIG. 17. Methods of pre-stressing or pre-treating the reinforcement layer 22 include, but are not limited to, fatiguing, heat treating, chemical treating, pinching, crushing, nicking, etc. the braids or mesh of the reinforcement layer 22 in a line corresponding to the location of the gaps 48a. Another method of pre-stressing or pre-treating includes cutting the braids or mesh 22 at intervals along the line corresponding to the location of the gaps 48a.

In one embodiment, the braids or mesh 22 are configured to resist forces tending to crush, kink, twist, longitudinally compress, or longitudinally stretch the tubular body 10, but are also configured to fail in the vicinity of the separation line 26 when sides of the wall structure 18 opposite from each other across the separation line 26 are forced laterally apart from each other. Thus, the reinforcement layer 22 allows the tubular body 10 to be both splitable/peelable and able to resist the forces typically exerted on the tubular body 10 when utilized during a medical procedure.

In one embodiment, the pre-stressing or pre-treating of the reinforcement layer 22 takes place prior to the placement of the of the reinforcement layer 22 about the inner tube sections 40a, 40b. The lines of pre-stressing or pre-treating are then aligned with the gaps 48 when the reinforcement layer 22 is placed about the inner tube sections 40a, 40b. In another embodiment, the pre-stressing or pre-treating of the reinforcement layer 22 takes place after the reinforcement layer 22 is placed about the inner tube sections 40a, 40b.

Figure 18:
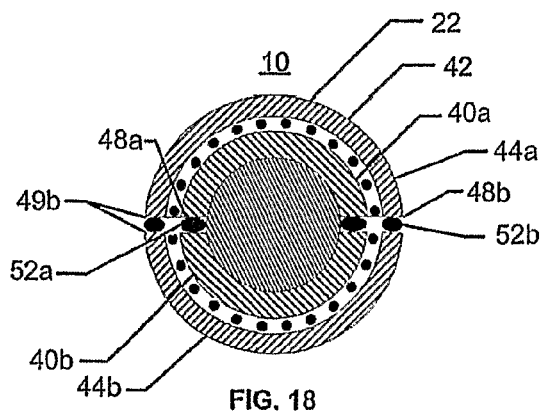
FIG. 18 is the same view depicted in FIG. 17, except a pair of outer tube sections has been disposed about the outer circumferential surface of the reinforcement layer.

As shown in FIG. 18, two outer tube sections 44a, 44b, which are similar in thickness and material to those previously described in this Detailed Description, are placed over the reinforcement layer 22 such that the gaps 48b formed by the outer tube sections 44a, 44b align with the gaps 48a formed by the inner tube sections 40a, 40b [block 408]. The gaps 48b are defined by edges 49b of the outer tube sections 44a, 44b. Extruded sections 52b, which are similar in configuration and material to those previously described in this Detailed Description, are placed in the gaps 48b formed between the outer tube sections 44a, 44b [block 410].

Figure 19:
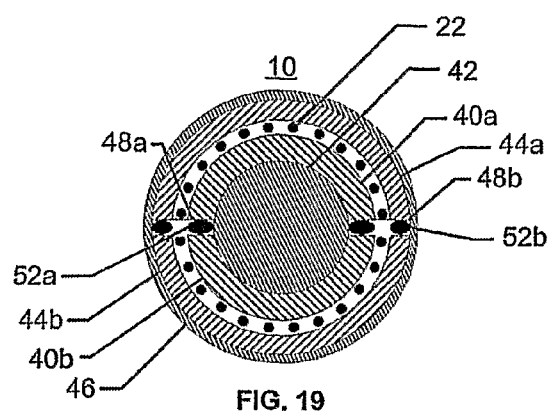
FIG. 19 is the same view depicted in FIG. 18, except a heat shrink tube has disposed about the outer circumferential surface of the outer tube sections.
Figure 20:
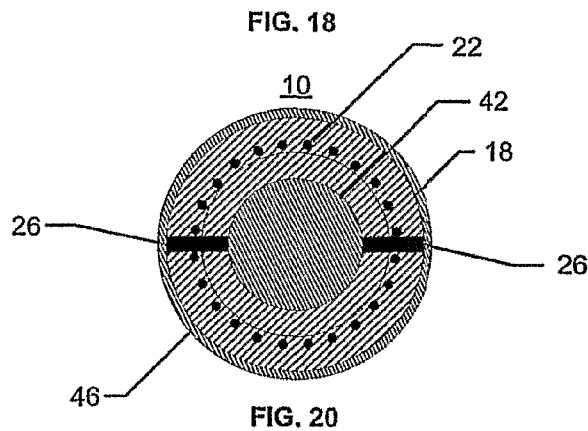
FIG. 20 is the same view depicted in FIG. 19, except heat has been applied to heat shrink the outer tube sections about the inner tube sections and reinforcement layer to form a flexible tubular body with an integral wall structure.

As shown in FIG. 19, a shrink tube 46, which is similar in thickness and material to those previously described in this Detailed Description, is placed snuggly over the outer circumferential surface of the assembly comprising the mandrel 42, the inner tube sections 40a, 40b, the reinforcement layer 22, the outer tube sections 44a, 44b, and the polymer extrusions 52a, 52b [block 412]. Heat is then applied to the shrink tube covered assembly, as previously discussed. This causes the outer tube sections 44a, 44b to impregnate the reinforcement layer 22 and bond with the inner tube sections 40a, 40b. The heat also causes the extrusions 52a, 52b to bond with the inner and outer tube sections 40a, 40b, 44a, 44b to form the separation lines or strips 26. The result of applying heat to the assembly is a flexible tubular body 10 having an integral wall structure 18 with separation lines 26 formed by the border/interfaces between the polymer extrusions 52a, 52b and the tube sections 40a, 40b, 44a, 44b, as indicated in FIG. 20 [block 414].

Figure 21:
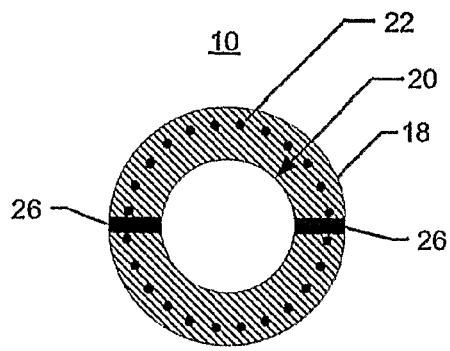
FIG. 21 is the same view depicted in FIG. 20, except the heat shrink tube has been removed from the flexible tubular body and said body has been removed from the mandrel.

As shown in FIG. 21, the shrink tube 46 is then removed from the resulting flexible tubular body 10, which has a reinforced wall structure 18 that is readily separable along a separation line or strip 26 [block 416].

For a discussion of a method of manufacturing another version of the second embodiment of the tubular body 10, reference is now made to FIGS. 22-27 and 29. FIGS. 22-27 are latitudinal cross-sectional elevations of the tubular body 10 at various stages of the manufacturing process as if taken along section line AA in FIG. 1. FIG. 29 is a block diagram outlining the method pertaining to FIGS. 22-27.

Figure 22:
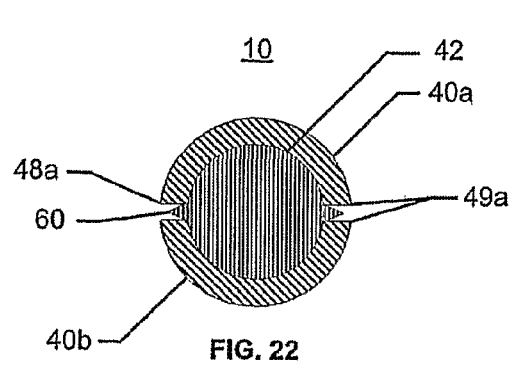
FIG. 22 is a latitudinal cross-sectional elevation of a pair of inner tube sections of the tubular body as the body is being manufactured on a mandrel having ridges and as if taken along section line AA in FIG. 1.

As shown in FIG. 22, an inner tube 40 of a flexible tubular body 10 is placed over a mandrel 42 [block 500]. In one embodiment, the inner tube 40 will have a single cut or gap 48a running the length of the tube 40. In another embodiment, the inner tube 40 will have two or more cuts or gaps 48a forming two or more inner tube sections 40a, 40b. For example, as illustrated in FIG. 22, where an inner tube 40 has two cuts or gaps 48a, the inner tube 40 will comprise two inner tube sections 40a, 40b. The gaps 48a are defined by edges 49a of the inner tube sections 40a, 40b.

As indicated in FIG. 22, the mandrel 42 includes ridges 60 that extend into the gaps 48a between the ends of the two inner tube sections 40a, 40b. The ridges 60 are used to form peel grooves 62 in the completed tubular body 10.

Figure 23:
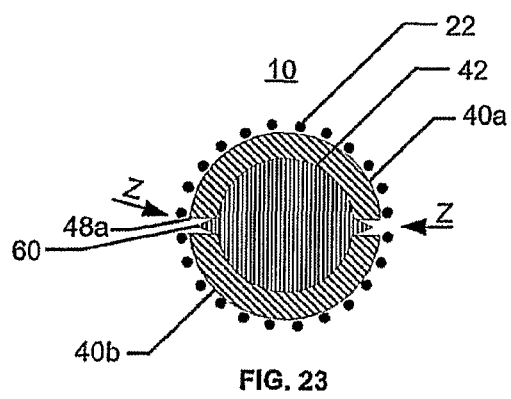
FIG. 23 is the same view depicted in FIG. 22, except a reinforcement layer has been disposed about the outer circumferential surface of the inner tube sections.

As shown in FIG. 23, a reinforcement layer 22, which is similar in configuration and material to those previously described in this Detailed Description, is slid over or wound/wrapped about the outer circumferential surface of the inner tube sections 40a, 40b [block 502]. In one embodiment, the reinforcement layer 22 is pre-stressed or pre-treated, by any one of the methods previously described in this Detailed Description, to fail along a line on the reinforcement layer 22 that corresponds and aligns with the separation line 26 to be formed in the tubular body 10 [block 504]. In other words, the reinforcement layer 22 is pre-stressed or pre-treated to fail in the area identified by each arrow Z in FIG. 23.

In one embodiment, the pre-stressing or pre-treating of the reinforcement layer 22 takes place prior to the placement of the of the reinforcement layer 22 about the inner tube sections 40a, 40b. The lines of pre-stressing or pre-treating are then aligned with the gaps 48 when the reinforcement layer 22 is placed about the inner tube sections 40a, 40b. In another embodiment, the pre-stressing or pre-treating of the reinforcement layer 22 takes place after the reinforcement layer 22 is placed about the inner tube sections 40a, 40b.

Figure 24:
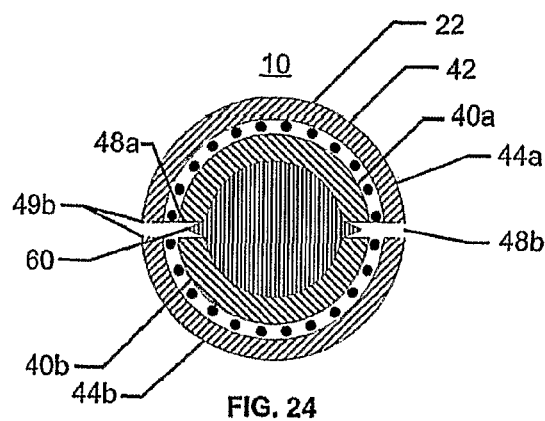
FIG. 24 is the same view depicted in FIG. 23, except a pair of outer tube sections has been disposed about the outer circumferential surface of the reinforcement layer.

As shown in FIG. 24, two outer tube sections 44a, 44b, which are similar in thickness and material to those previously described in this Detailed Description, are placed over the reinforcement layer 22. The two outer tube sections 44a, 44b are positioned such that the gaps 48b formed by the outer tube sections 44a, 44b align with the gaps 48a formed by the inner tube sections 40a, 40b [block 506]. The gaps 48b are defined by edges 49b of the outer tube sections 44a, 44b.

Figure 25:
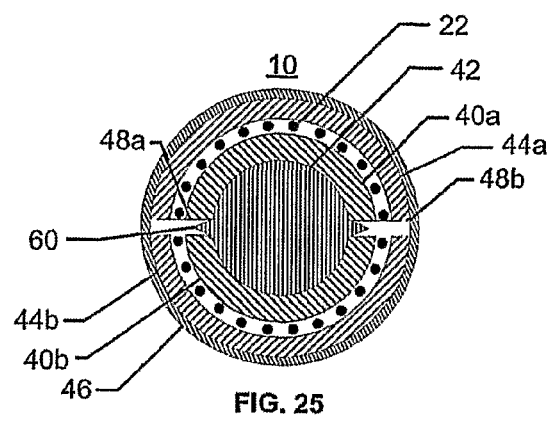
FIG. 25 is the same view depicted in FIG. 24, except a heat shrink tube has disposed about the outer circumferential surface of the outer tube sections.
Figure 26:
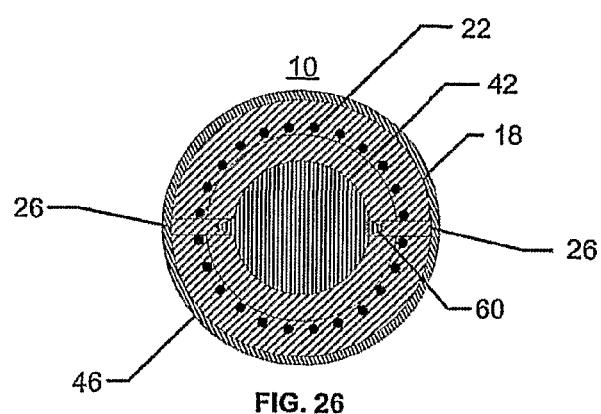
FIG. 26 is the same view depicted in FIG. 25, except heat has been applied to heat shrink the outer tube sections about the inner tube sections and reinforcement layer to form a flexible tubular body with an integral wall structure having peel grooves.

As shown in FIG. 25, a shrink tube 46, which is similar in thickness and material to those previously described in this Detailed Description, is placed snuggly over the outer circumferential surface of the assembly comprising the mandrel 42, the inner tube sections 40a, 40b, the reinforcement layer 22, and the outer tube sections 44a, 44b [block 508]. Heat is then applied to the shrink tube covered assembly, as previously discussed. This causes outer tube sections 44a, 44b to impregnate the reinforcement layer 22 and bond with the inner tube sections 40a, 40b. The heat also causes the inner and outer tube sections 40a, 40b, 44a, 44b to reflow such that the gaps 48a, 48b cease to exist as the tube sections 40a, 40b, 44a, 44b melt together. The result of applying heat to the assembly is a flexible tubular body 10 having an integral wall structure 18 with separation lines 26 formed by the ridges 60 of the mandrel 42, as indicated in FIG. 26 [block 510].

Figure 27:
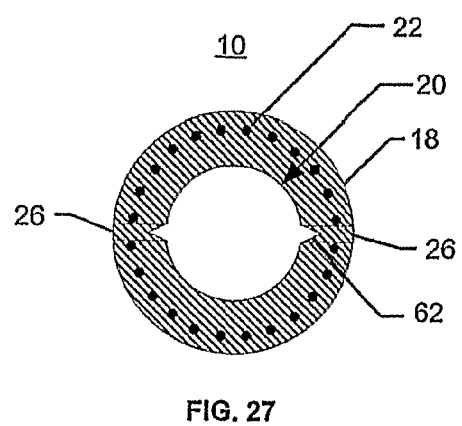
FIG. 27 is the same view depicted in FIG. 26, except the heat shrink tube has been removed from the flexible tubular body and said body has been removed from the mandrel.

As shown in FIG. 27, the shrink tube 46 is then removed from the resulting flexible tubular body 10, which has a integral reinforced wall structure 18 that is readily separable along a separation line 26 defined by peel groove 62 formed by the ridges 60 of the mandrel [block 512].

In use, a puncture is made with a thin walled needle through the skin and into a blood vessel. A guidewire is then placed through the needle into the blood vessel and the needle is withdrawn. An intravascular introducer is advanced over the guidewire into the lumen of the blood vessel. The tubular body 10 is inserted into the introducer and manipulated so it travels along the blood vessel to the point of treatment (e.g., a chamber in the heart). The travel and positioning of the tubular body 10 within the patient is monitored via X-ray fluoroscopy.

A medical device (e.g., pacemaker lead) is inserted through the lumen 20 of the tubular body 10 to the point of treatment. Once the device is positioned and implanted within the patient, the tubular body 10 will be removed. However, to clear the pacemaker lead, the tubular body 10 will need to be split/peeled along the separation line 26. This is done by laterally forcing apart sides of the wall structure 18 that are opposite from each other across the separation line 26. This forcing apart causes the wall structure 18 to split/peel along the separation line 26. Once the tubular body 10 has been split/peeled, the pacemaker lead can be cleared and the tubular body 10 can be removed from the patient without displacing the pacemaker lead.

Although the present invention has been described with reference to preferred embodiments, persons skilled in the art will recognize that changes may be made in form and detail without departing from the spirit and scope of the invention.

We claim:

1. A splittable reinforced flexible tubular body for a catheter or sheath, the body comprising:
   a proximal end;
   a distal end;
   a wall structure extending between said ends and including a reinforcement layer within said wall structure and a separation line extending longitudinally along the wall structure and adapted to facilitate the splitting of the wall structure; and
   a lumen defined by said wall structure,
   wherein the reinforcement layer is formed without introducing discontinuities thereto and extends substantially from the proximal end of the body to the distal end of the body.

2. The body of claim 1, wherein the reinforcement layer is a mesh or braid layer.

3. The body of claim 1, wherein the separation line is a strip of a first polymer material that is different from a second polymer material utilized to form the rest of the wall structure.

4. The body of claim 3, wherein a bond interface between the first and second polymer materials creates a stress concentration that facilitates the splitting of the wall structure.

5. The body of claim 3, wherein the first polymer material is more radiopaque than the second polymer material.

6. The body of claim 5, wherein the first polymer material is a polymer loaded with biocompatible radiopaque filler of pure metal or metallic compound with at least one atomic number of from about 22 to about 83.

7. The body of claim 5, wherein the first polymer material is a polymer loaded with tungsten.

8. The body of claim 3, wherein the separation line is formed by severing the wall structure to form a longitudinally extending gap, inserting the strip of first polymer material into the gap, and causing the first polymer material to bond to the second polymer material.

9. The body of claim 3, wherein the reinforcement layer is pre-stressed or pre-treated without being severed to fail along a longitudinal path that aligns with the separation line.

10. The body of claim 1, wherein the separation line is defined by a peel groove longitudinally extending along the wall structure.

11. The body of claim 10, wherein the separation line is formed by severing the wall structure to form a longitudinally extending gap, aligning said gap with a peel groove forming feature on a mandrel, and heating the wall structure to cause the wall structure to rejoin at the gap while forming a peel groove.

12. The body of claim 10, wherein the reinforcement layer is pre-stressed or pre-treated without being severed to fail along a longitudinal path that aligns with the separation line.

* * * * *